United States Patent
Laakkonen et al.

(10) Patent No.: US 12,042,258 B2
(45) Date of Patent: Jul. 23, 2024

(54) APPARATUS AND METHOD FOR MEASURING PHOTOPLETHYSMOGRAM

(71) Applicant: Oura Health Oy, Oulu (FI)

(72) Inventors: Harri Matti-Heikki Laakkonen, Oulu (FI); Hannu Olavi Kinnunen, Oulu (FI); Markku Olavi Koskela, Oulu (FI)

(73) Assignee: Oura Health Oy, Oulu (FI)

( * ) Notice: Subject to any disclaimer, the term of this patent is extended or adjusted under 35 U.S.C. 154(b) by 85 days.

(21) Appl. No.: 17/681,571

(22) Filed: Feb. 25, 2022

(65) Prior Publication Data

US 2022/0296117 A1    Sep. 22, 2022

Related U.S. Application Data

(62) Division of application No. 14/606,341, filed on Jan. 27, 2015, now Pat. No. 11,291,378.

(51) Int. Cl.
*A61B 5/024* (2006.01)
*A61B 5/00* (2006.01)
*A61B 5/1455* (2006.01)

(52) U.S. Cl.
CPC ........ *A61B 5/02433* (2013.01); *A61B 5/6826* (2013.01); *A61B 5/7217* (2013.01)

(58) Field of Classification Search
None
See application file for complete search history.

(56) References Cited

U.S. PATENT DOCUMENTS

| | | | |
|---|---|---|---|
| 2012/0203077 A1 | 8/2012 | He et al. | |
| 2013/0324855 A1* | 12/2013 | Lisogurski | A61B 5/14551 600/476 |
| 2014/0275852 A1* | 9/2014 | Hong | A61B 5/0002 600/479 |
| 2015/0018654 A1 | 1/2015 | Mestha et al. | |

FOREIGN PATENT DOCUMENTS

| | | | | |
|---|---|---|---|---|
| WO | 2013190423 A1 | 12/2013 | | |
| WO | WO-2013190423 A1 * | 12/2013 | | A61B 5/02416 |

* cited by examiner

*Primary Examiner* — Patricia J Park
(74) *Attorney, Agent, or Firm* — Holland & Hart LLP

(57) ABSTRACT

Disclosed is an apparatus for measuring photoplethysmogram. The apparatus includes a ring structure with at least one photon source and at least one photon detector positioned on an inner surface of the ring structure. The apparatus further includes a controller configured to measure a preliminary photoplethysmogram during a first time period by taking a first number of samples, determine a form factor from said preliminary photoplethysmogram, determine an inter beat interval from said preliminary photoplethysmogram, and use the form factor and the inter beat interval to determine a second number of samples to be taken during a second time period of measurement of the photoplethysmogram and the distribution of the samples to be taken in function of time.

6 Claims, 3 Drawing Sheets

APPARATUS AND METHOD FOR MEASURING PHOTOPLETHYSMOGRAM

CROSS REFERENCE

The present application for patent is a divisional of U.S. patent application Ser. No. 14/606,341 by Laakkonen et al., entitled "Apparatus and Method for Measuring Photoplethysmogram" filed Jan. 27, 2015, each of which are expressly incorporated by reference in its entirety herein.

FIELD OF TECHNOLOGY

The present disclosure generally relates to analysing and processing of biological signals, and, more specifically, to an apparatus and a method for measuring a photoplethysmogram.

BACKGROUND

Recent consumer's interest in personal health has led to a variety of personal health monitoring devices being offered on the market. For example, wearable devices for monitoring personal health are well known in the art. One such example includes a device, which uses photoplethysmogram (PPG) technology for deriving various health monitoring related information such as respiration, pulse, oxygen saturation, user's movement and the like. A PPG is often obtained by using a pulse oximeter which illuminates the skin and measures changes in light absorption. A pulse oximeter monitors the perfusion of blood to the dermis and subcutaneous tissue of the skin.

Typically, a PPH measurement setup (oximeter) uses at least one photon emitting diode (LED) and a photodiode configured to receive reflected LED light from the at least one LED. The at least one LED and the photodiode both are configured to be in contact with the user's skin. Therefore, there exists a possibility that user's movement may cause the LED to move or sift from its desired position, which may result in addition of ambient light to the photodiode while collecting the reflected LED light. The ambient light may cause artifacts in the PPG signals, which is generally addressed by using a direct current (DC) offset technique. However, the DC offset should be applied tactfully on the PPH signals since such adjustment can distort the signal quality. Further, such wearable devices are battery operated, and electronic components therefor, mainly, the LED and photodiode, consume substantial amount of electrical energy during operation. Moreover, such devices are configured to operate continuously, i.e. to continuously monitor and measure user's health parameters. This requires either use of a powerful or heavy duty battery or quick replacement of battery for the continuous operation of such devices.

Therefore, in light of the foregoing discussion, there exists a need to overcome the aforementioned drawbacks of power efficient operation of such devices and application of DC offset without distorting signal quality while measuring PPH.

SUMMARY

The present disclosure seeks to provide an apparatus for measuring photoplethysmogram.

The present disclosure also seeks to provide a method for measuring photoplethysmogram.

In one aspect, an embodiment of the present disclosure provides an apparatus for measuring photoplethysmogram, the apparatus comprising:
a ring structure with at least one photon source and at least one photon detector positioned on an inner surface of the ring structure; and a controller configured to measure a preliminary photoplethysmogram during a first time period by taking a first number of samples, determine a form factor from said preliminary photoplethysmogram, determine an inter beat interval from said preliminary photoplethysmogram, and use the form factor and the inter beat interval to determine a second number of samples to be taken during a second time period of measurement of the photoplethysmogram and the distribution of the samples to be taken in function of time.

In another aspect, an embodiment of the present disclosure provides a method for measuring photoplethysmogram. The method comprises steps of:
measuring a preliminary photoplethysmogram during a first time period by taking a first number of samples;
determining a form factor from said preliminary photoplethysmogram;
determining an inter beat interval from said preliminary photoplethysmogram;
using the form factor and the inter beat interval to determine a second number of samples to be taken during a second time period of measurement of the photoplethysmogram and the distribution of the samples to be taken in function of time.

Embodiments of the present disclosure substantially eliminate or at least partially address the aforementioned problems in the prior art and provides an apparatus and a method for measuring photoplethysmogram using an adaptive sampling rate.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein.

Figure 1:
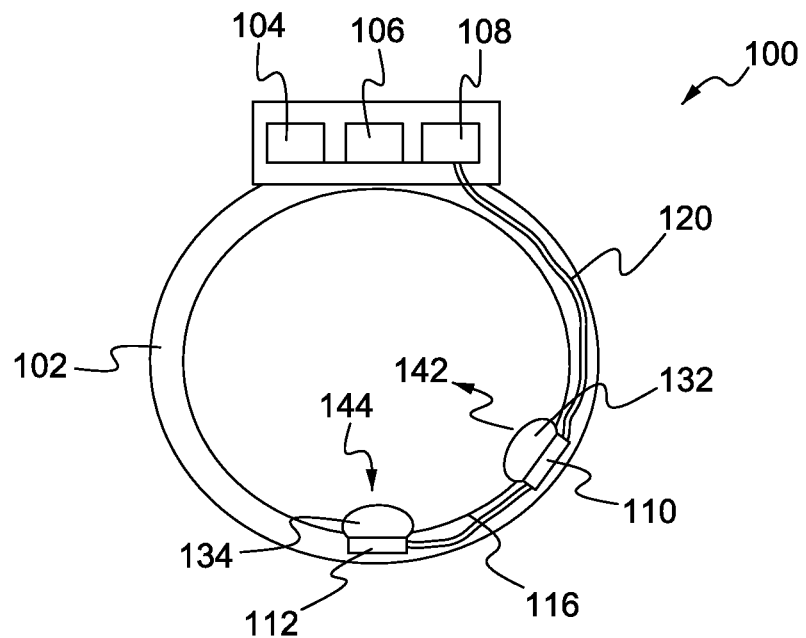
FIG. 1 is a schematic illustration of an apparatus for measuring photoplethysmogram, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

In one aspect, an embodiment of the present disclosure provides an apparatus for measuring photoplethysmogram comprising:
- a ring structure with at least one photon source and at least one photon detector positioned on an inner surface of the ring structure; and
- a controller configured to
    - measure a preliminary photoplethysmogram during a first time period by taking a first number of samples,
    - determine a form factor from said preliminary photoplethysmogram,
    - determine an inter beat interval from said preliminary photoplethysmogram, and
    - use the form factor and the inter beat interval to determine a second number of samples to be taken during a second time period of measurement of the photoplethysmogram and the distribution of the samples to be taken in function of time.

In an embodiment, the apparatus is a wearable device configured to be worn on a finger of a user. For example, the ring structure of the apparatus is sized to be suitably worn at a finger, such as an index finger, of the user. The ring structure, particularity, an inner portion (configured to contact user's finger) is made a material that prevents sliding or slipping of the apparatus from the user's finger.

In another embodiment, the apparatus may be configured to be worn at a wrist of the user. In such instance, it may be evident to those skilled in the art that a size of the ring structure should be large enough to be suitably worn at the wrist of the user.

The apparatus is operable to monitor and measure biological signals, such as blood volume pulse, to determine a heart rate of the user. Specifically, the heart rate is determined by measuring PPG from the blood volume pulse. The PPG can be measured or generated using optical electronics, particularity using the principle of transmittance or reflectance of light. As mentioned above, the apparatus includes optical electronics, which includes at least one photon source and at least one photon detector positioned on an inner surface of the ring structure. In an example, the at least one photon source is infrared light (IR) emitting diode and the at least one photon detector is IR receiving diode (such as photon diode or photon transistor).

The apparatus may also comprise further photon sources and/or photon detectors, such as a second photon source located symmetrically on the other side of the photon detector, with respect to the other photon source. Such a system may be optimized such that it uses the photon source that gives better amplitudes. Alternatively, one photon source is used in period of high activity and the other in period of low activity. The two or more photon sources may also emit different wavelengths.

The apparatus also includes other electronic components apart from the IR emitting or receiving diodes. For example, the apparatus includes electronic components such as a microprocessor, a controller, memories and a communication module. The controller is operable to control the at least one photon source and to receive measurement information from the at least one photon detector. In an example, the at least one photon source and the at least one photon detector is connected to a controller by a flexible printed circuit board.

The apparatus also includes optical components, such as lens elements arranged on the ring structure for covering the at least one photon source and the at least one photon detector underneath. The lens element covering the at least one photon source allows the light emitted or generated by the at least one photon source to pass there-through. Similarly, the lens element covering the at least one photon detector allows the reflected light to pass there-through for being collected by the at least one photon detector. The light collected by the at least one photon detector is the reflected light from blood vessels of either the finger or the wrist (depending where the apparatus is worn). The photon source (such as a LED) and the photon detector may also in themselves comprise as an integral part a lens part that functions as an optical component. The lens part may be in the form of a dome, that increase the surface of contact between the skin and the apparatus, to improve sensitivity of the measurement.

In an embodiment, when the apparatus is worn on the user's finger the optical electronics thereof should be able to acquire appropriate measurement data (i.e. blood volume pulse). Specifically, the lens element (covering the at least one photon source) should contact at least a common digital artery or a palmar metacarpal artery of the user's finger for collecting appropriate measurement data. For example, an IR light pulse can be sent from the at least one photon source and thereafter reflected IR light can be received by the at least one photon detector. Further, the variations in volume of the blood vessels (during the flow of blood) result in variation in the measured transmission (i.e. IR light intensity) which is measured and processed to generate the PPG.

As mentioned above, the controller is operable to control the at least one photon source and to receive measurement information from the at least one photon detector. For example, the controller includes a driving circuit operable to control the at least one photon source and an amplification circuit operable to optimize received measurement information from the at least one photon detector. Typically, the driving circuit instructs the at least one photon source to illuminate (which is further explained in greater detail herein later) for directing a photon pulse towards blood vessels of the user's finger (or the wrist). Thereafter, the reflected light pulse from the blood vessels is collected by the at least one photon detector for being received by the amplification circuit for further processing.

In an embodiment, when the at least one photon detector may collect additional light in addition to the reflected light pulse from the blood vessels, artifacts that may be caused by the ambient light is addressed by using a DC offset technique. The additional light can be an ambient light present around the user. Otherwise, the additional light can be any other form of light that the photon detector is subjected to due to user's surrounding.

In an embodiment, the DC offset is applied on the measured signals (from the at least one photon detector) with the help of the amplification circuit of the controller. Specifically, the controller includes at least one amplifier operatively coupled to the amplification circuit for amplifying measured signals from the at least one photon detector. The term "amplifying" used herein means both increasing and decreasing measured signal parameters (such as amplitude).

In an embodiment, when the ambient light conditions are "brighter" the amplification circuit is set to lower (optimize) an output signal level from the least one photon detector. For example, the amplification circuit uses measurement signal level at point 1 (first time) to adjust a first amplifier value to a desired average output level. The desired average output level can be a predetermined measurement level, associated with the collected reflected light pulse, to be measured by the at least one photon detector. In an example, the predetermined measurement level may be defined in amperes or volts per watt of reflected light, which is a responsivity of the at least one photon detector.

In another embodiment, the output from the first amplifier is further amplified with a second amplifier. Specifically, the output of the first amplifier is measured at point 2 (second time) with the amplification circuit; thereafter the amplification circuit uses the measurement information at point 2 to further adjust or optimize the second amplifier value to the desired average output level. The amplification circuit accordingly uses a series of amplifiers configured to output the desired average output level corresponding to the collected reflected light. As is evident to those skilled in the art, the controller may include any number of amplifiers, apart from two amplifiers, such as one amplifier, three or four amplifiers, for amplifying the measured level of the at least one photon detector.

The output signal from the second amplifier is further routed to an analogue to digital (AD) converter for generating digital signal from the analogue signal (i.e. measurements of the at least one photon detector). In the present embodiment, the amplification circuit enables to keep an average output level (DC level) from the second amplifier at a midpoint range of the AD converter. Accordingly, the artifacts that may be caused by the ambient light is addressed by the DC offset technique mentioned herein.

Further, based on above, a need for having a large range AD converter may be eliminated. Specifically, as the average output level (DC level) from the second amplifier is provided at the midpoint range of the AD converter, in such instance even a small range AD converter provides a sufficient resolution for digital signal. For example, an 8 bit AD converter may be used instead of a 16 bit AD for converting the analogue signal into digital signal. This in turn enables in saving battery power of the apparatus since power required for AD conversion by a large range AD converter (16 bit) is more as compared to a small range AD converter (8 bit). The digital signal or information is further routed to the microprocessor for processing and/or to the memory for being stored. Specifically, the digital signals are processed to generate the PPG, which can be used for derive health monitoring related information, such as a heart rate, of the user.

In one embodiment (as mentioned above), from a PPG (represented by a pulse waveform) a heart rate of the user can be determined by calculating a time period between two peaks of the pulse waveform. For example, if the heart rate is 120 beats per minute, time between two peaks is about 60/120=500 msec, which is referred to as inter beat interval (IBI).

In an embodiment, the apparatus of the present disclosure, particularly, the controller of the apparatus is operable to make the measurements of the PPG by following a particular set of steps. For example, the controller initially measures PPG for a first time period to determine a form factor. Specifically, to initiate the function of the apparatus, the controller measures sample PPG signals for the first time period, which can be from few seconds to tens of seconds.

The controller measures the PPG signals for the first time period, such that sufficient sampling information (PPG signal) is captured, i.e. to have a well-defined and consistent form factor for the measured PPG signal. In other words, during the first time period sufficient sample measurements (number of times the at least one photon source is illuminated or turned ON) are taken such that the form factor of the PPG signal is well defined.

In an example, the first time period could be 10 seconds. Further, with a measurement rate of 1 millisecond (msec) in a time interval of 5 msec, the first time period of 10 second takes (10 sec/5 msec) 2000 samples or measurements. Therefore, during the first time period a total duration of measuring time ('ON' time for the at least one photon source) is 1 msec×2000=2 sec.

The controller thereafter determines an IBI from the form factor. Specifically, a time between two peaks of a pulse waveform of the PPG signal is measured for determining the IBI. For example, if the user is having a heart rate of 120 beats per minute the IBI would be about 60/120=500 msec.

According to an embodiment, the form factor and the inter beat interval are used for determining a probability function, which probability function further defines the distribution of the samples to be taken during the second period of measurement. The controller thus further determines a probability function related to the form factor using the IBI. The probability function is primarily based on the form factor, i.e. where it is likely to have peaks of the pulse waveform. Therefore, the probability function (for a consistent pulse waveform of the PPG signal) would be periodic in nature. Further, based on the periodic nature, the probability function may have a waveform of uniform shape such as a triangular waveform, a sinusoidal waveform, a square waveform or an arbitrary shape waveform which can be a combination of the triangular, sinusoidal and square waveforms.

Further, due to the periodic nature of the probability function, the waveform thereof, may have a frequency, i.e. f=1/IBI. It may be evident to those skilled in the art that the frequency (and a form factor of the probability function) may change based on a change in the heart rate of the user. This helps in considering the variation in heart rate (i.e. changes in IBI) during further measurement of the PPG.

As mentioned above, the controller determines the probability function, particularly, the probability function is selected to result in more samples to be taken from peaks of the PPG compared to other parts of the PPG. Specifically, the probability function relates to a sampling rate, i.e. number of samples to be taken at various points of a PPG signal based on the pulse waveform of the probability function. The number of samples to be taken relates to the number of times the at least one photon source should be illuminated while measuring the PPG.

In an embodiment, a high probability is assigned around likely peaks of the pulse waveform of the probability function, i.e. the sampling rate should be higher at such points as compared to other points of the pulse waveform. For example, a probability of 1 can be assigned around likely peaks, a probability of 0.1 can be assigned around likely bottoms and a probability of 0.5 can be assigned for likely middles (between the peaks and the bottoms) points of the waveform. This way a larger number of measurement samples are collected for the peaks of the pulse waveform of the probability function as compared to bottoms or middles of the waveform. Further, based on the probability function a sampling rate can be assigned to the subsequent pulse waveform of PPG, i.e. for the subsequent measurement of the PPG.

In an embodiment, the driving circuit of the controller is operable based on the probability function for controlling a function of the at least one photon source while measuring the PPG.

The controller therefore using the probability function determines number of samples to be measured during a second time period of measurement of the PPG, i.e. the controller is further configured to adjust the second number of samples to be taken during a second time period of measurement of the photoplethysmogram and the distribution of the samples to be taken in function of time, if the inter beat interval changes. For example, based on the probability function a number of samples to be taken for subsequent time periods (while measuring the PPG) are determined. The number of samples to be taken may change for the subsequent time periods (while measuring the PPG) based on the IBI. For example, the IBI can fall or rise in the subsequent time periods. Therefore, the sampling rate should be accordingly changed for the future pulse waveform. In an example, when the IBI increases, the sampling rate should be decreased, similarly, and when the IBI decreases the sampling rate should be increased. Accordingly, the apparatus of the present disclosure based on the probability function dynamically and continuously changes the number of samples to be taken for the measurement of the PPG.

As mentioned above, the controller of the apparatus is operable to apply DC offset on the measured signals (from the at least one photon detector). In an embodiment, the controller of the apparatus is further configured to dynamically bias the direct current (DC) offset during an off-peak time period of the photoplethysmogram. Specifically, the DC offset adjustment is done at low probability values, i.e. at bottoms of the pulse waveform of the probability function, without distorting the signal quality during the peaks of the PPG. This way improved PPG can be measured.

In an embodiment, the measurement results during the second time period are further filtered using the probability function. For example, the probability function can be used to filter measured data to reduce artifacts such as double peak structures.

In an embodiment, the measured PPG can be displayed to the user. For example, the apparatus may include an electronic display for displaying the measured PPG. Otherwise, the apparatus may be operable to communicably couple with an electronic device, having a display, such as a smart phone, a tablet, a laptop and the like, for displaying the measured PPG. It may be evident to those skilled in the art that the apparatus may be communicably coupled to such electronic devices using the communication module, such as Bluetooth, Wifi, and the like.

In another aspect, an embodiment of the present disclosure provides a method for measuring photoplethysmogram. The method comprising the steps of:
  measuring a preliminary photoplethysmogram during a first time period by taking a first number of samples;
  determining a form factor from said preliminary photoplethysmogram;
  determining an inter beat interval from said preliminary photoplethysmogram; using the form factor and the inter beat interval to determine a second number of samples to be taken during a second time period of measurement of the photoplethysmogram and the distribution of the samples to be taken in function of time. Further, the method may comprise a step of using the form factor and the inter beat interval for determining a probability function, which probability function further defines the distribution of the samples to be taken during the second period of measurement. According to another embodiment, the probability function is determined to result in more samples taken from peaks of the photoplethysmogram compared to other parts of the photoplethysmogram. The method may still further comprise a step of dynamically biasing direct current offset during an off-peak time period of the photoplethysmogram. Optionally, the method also comprises adjusting the second number of samples to be taken during a second time period of measurement of the photoplethysmogram and the distribution of the samples to be taken in function of time, if the inter beat interval changes. Still further, the measurement results during the second time period can be filtered using the probability function.

According to an embodiment, as explained above a use of adaptive sampling rate i.e. the number of samples to be taken based on the probability function, makes the operation of the present apparatus substantially power efficient. The improved power efficiency of the apparatus is shown with a following example calculation. The calculation includes few assumption, which are as follows:
  1) The battery of the apparatus has power or capacity of 40 milliampere hour (mAh)
  2) The optical electronics of the apparatus, i.e. the at least one photon source (IR emitting diode), the at least one photon detector (IR receiving diode), AD converter, amplifiers, memories and the like, use total of 19 mA of power during a measurement cycle of 1 msec. Therefore, the 40 mAh battery can be used to make 40 mAh/19 mA/1 msec=7578947 measurements or samples.
  3) During 'OFF' time, particularly in a standby mode, the electronics of the apparatus uses 0.1 mA. Therefore, the apparatus can be in standby mode (with no measurements) for 40 mA/0.1 mA=400 hours.
  4) Further, a heart rate of the user is 120 beats per minute, i.e. IBI is 500 msec.
  5) Moreover, a sampling rate is 1 msec ON time and 4 msec OFF time.

Based on the above assumption, following calculation seniors are possible:
  A) If the measurement is ON all the time (measurements or samples are taken continuously for the PPG) the battery will last for 40 mA/19 mA=2.1 hours.

B) If the measurement is made intermittently with a duty cycle of 1 msec ON time and 4 msec OFF time. The average usage or power consumption of the battery of apparatus during a cycle would be 19 mA×⅕+0.1 mA×⅘=3.88 mA, therefore battery will last for 40 mA/3.88 mA=10.3 hours.

C) Using the adaptive sampling rate (the number of sample to be taken determined based on the probability function related to the form factor using the IBI) of the present disclosure, i.e. with probability distribution of measuring with p=1 for t=100 msec at peak proximity of the pulse wave form, with p=0.1 for t=100 msec at bottom proximity of the pulse wave form, and with p=0.5 for 300 msec for the middle (between the peak and the bottom) of the pulse waveform, the following number of measurements or samples would be taken:

Number of measurements/samples=time×sampling rate where, sampling rate=s_max×p, and s_max is maximum sampling rate, for example 1 measurement every 5 msec (i.e. ⅕ measurement per msec), therefore During the peak time, 100×⅕×1=20 measurements are made During the bottom time, 100×⅕×0.1=2 measurements are made. During the middle time, 300×⅕×0.5=30 measurements are made.

Therefore, during the entire cycle of 500 msec only 52 measurements are made. Accordingly, total "ON" time is 52×1 msec=52 msec, and total OFF time is 500 msec-52 msec=448 msec. The power usage accordingly during the cycle of 500 msec is 19 mA×52 msec+0.1 mA×448 msec=1032.8 mAmsec. Therefore, the 40 mAh battery can make 40 mAh/1032.8 mAmsec=139426 measurements of the entire cycle. As one entire cycle takes 500 msec, 139426 cycles will take 139426×500 msec=19 hours. That means the apparatus (particularly the battery thereof) based on the present disclosure can have 19 hours of operational time.

Further, based on a form factor of the probability function the power saving for the apparatus can be significant. For example, when the form factor of the probability function is similar or consistent, in such instance, the PPG is measured with the samples being taken primarily for the peaks of the probability function, i.e. when p=1, and no samples are taken when p=0. In this way, the apparatus can take for example 50%, 80% or 90% less samples over time than using constant sampling rate. Accordingly, the power saving for the apparatus can be significant, and the apparatus still enable to get precise measurement data from proximity of the likely peaks of the PPG waveform.

The present disclosure provides an apparatus and a method for measuring photoplethysmogram, which can be used for deriving health monitoring related information such as a heartbeat of the user. The apparatus and method provide power efficient measurement of PPG. Specifically, the adaptive sampling rate (more samples taken from peaks of the PPG compared to other parts of the PPG) and use of a small range AD converter make the apparatus and method of the present disclosure power efficient. Further, the apparatus and method provide precise PPG without any artifacts since based on the adaptive sampling rate a sufficient number of measurements are taken for the peaks, bottoms and middle points of the PPG. Moreover, the apparatus and the method provide improved PPG without distorting signal quality. Specifically, the DC offset adjustment is done at low probability values, i.e. at bottoms of the pulse waveform of the probability function, without distorting the signal quality during the peaks of the PPG.

DETAILED DESCRIPTION OF THE DRAWINGS

Referring now to the drawings, particularly by their reference numbers FIG. 1 is a schematic illustration of an apparatus 100 for measuring photoplethysmogram, in accordance with an embodiment of the present disclosure. The apparatus 100 includes a ring structure 102. The apparatus 100 also includes a plurality of optical electronic elements for measuring PPG. For example, the apparatus 100 includes a microprocessor, memories and a communication module collectively shown with an element 104. The apparatus 100 also includes a battery 106 and a controller 108. The apparatus 100 also includes at least one photon source 110 and at least one photon detector 112 positioned in an inner surface 116 of the ring structure 102. The least one photon source 110 and the at least one photon detector 112 are operatively connected to the controller 108 by a flexible printed circuit board 120. The controller 108 is operable to control the at least one photon source 110 and to receive measurement value of the at least one photon detector 112.

The apparatus 100 also includes lens elements 132 and 134 covering the at least one photon source 110 and the at least one photon detector 112, respectively. The lens element 132 enables a photon pulse 142, generated by at least one photon source 110, to pass there-thought towards a finger of the user, when the apparatus 100 is worn in the finger. The lens element 134 enables a reflected light pulse 144 (of the photon pulse 142) to pass there-thought towards the at least one photon detector 112 for being collected. Specifically, the reflected light pulse 144 is reflected from blood vessels of the user's finger and carries blood volume pulses information.

Figure 2:
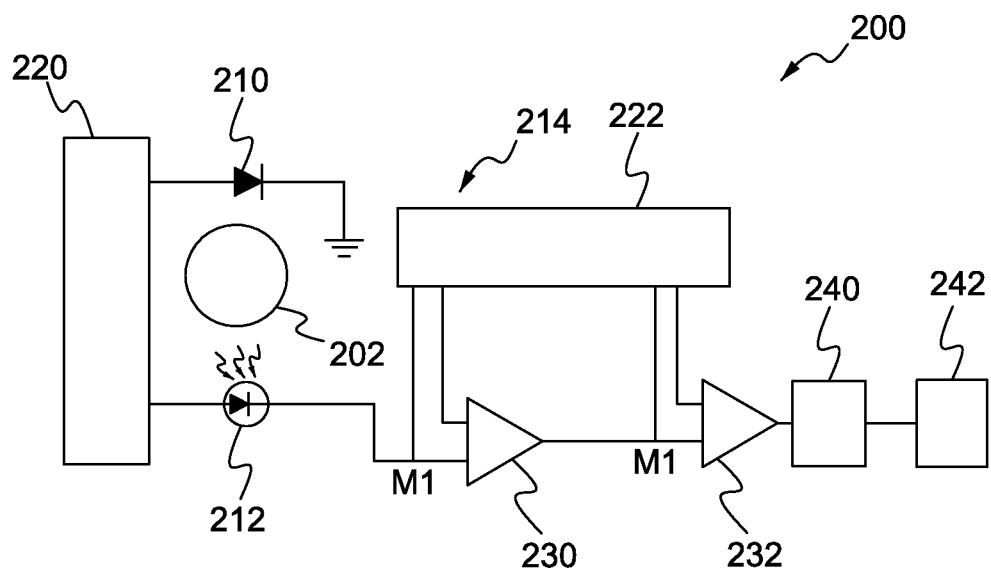
FIG. 2 is a schematic illustration of a measurement setup of the apparatus FIG. 1 for measuring a heart rate of a user, in accordance with an embodiment of the present disclosure.

Referring now to FIG. 2, shown is a schematic illustration of a measurement setup 200 of the apparatus 100 (of FIG. 1) for measuring a heart rate of the user, in accordance with an embodiment of the present disclosure. The measurement setup 200 enables in measuring the heart rate of the user from PPG signals based on the blood volume pulses of a user's finger 202. The measurement setup 200 includes an IR emitting diode 210 (such as the at least one photon source 110 of FIG. 1), an IR receiving diode 212 (such as the at least one photon detector 112 of the FIG. 1) and a controller 214 (such as the controller 108 of FIG. 1).

The controller 214 is operatively coupled to the IR emitting diode 210 and the IR receiving diode 212 to control the IR emitting diode 210 and to receive measurement value from the IR receiving diode 212. Specifically, the controller 214 includes a driving circuit 220 operable to control the IR emitting diode 210 and an amplification circuit 222 operable to optimize received measurement value from the IR receiving diode 212. The controller 214 also includes amplifiers 230, 232 operatively coupled to the amplification circuit 222.

The measurement setup 200 further includes an AD convertor 240 to receive analog measurement signals from the amplification circuit 222 to generate corresponding digital signals. The measurement setup 200 also includes a microprocessor 242 (such as the microprocessor of the FIG. 1) to receive the digital signals from the AD convector 240 for further processing and/or storing of the digital signals.

The driving circuit 220 is operable to control the operation (i.e. illumination and turning off) of the IR light emitting diode 210 for taking measurements or samples while measuring the PPG. Specifically, the driving circuit 220 is operable to control the operation of the IR emitting diode 210 to follow an adaptive sampling rate, i.e. number of samples taken based on a probability function related to a form factor of the PPG signals and the IBI, which is explained further in greater detail in conjunction with FIG. 3.

The amplification circuit 222 is operable to receive the measurement value from the IR receiving diode 212 for amplifying (i.e. increasing or decreasing the measurement value) and thereafter sending the amplified measurement value to the AD convector 240. Specifically, the measurement level from the IR receiving diode 212 is measured at a measurement point Ml with the amplification circuit 222. The amplification circuit 222 thereafter uses the measurement level at the point Ml to adjust the amplifier 230 to reach a desired average level. The output from the amplifier 230 is further amplified with the amplifier 232. Specifically, the output of the amplifier 230 is measured at a measurement point M2 with the amplification circuit 222. Thereafter, the amplification circuit 222 uses the measurement valve at the point M2 to adjust the amplifier 232 to output the desired average level. The amplification circuit 222 accordingly enables to output the desired average value level (i.e. DC level) from the amplifier 232 at a mid-point range of the AD converter 240. Further, the measurement value from the amplifier 232 is routed to the AD converter 240 for generating the corresponding digital signals. The digital signals can be finally processed by the microprocessor 242 to generate the PPG for acquiring the heart rate of the user from the PPG.

Figure 3:
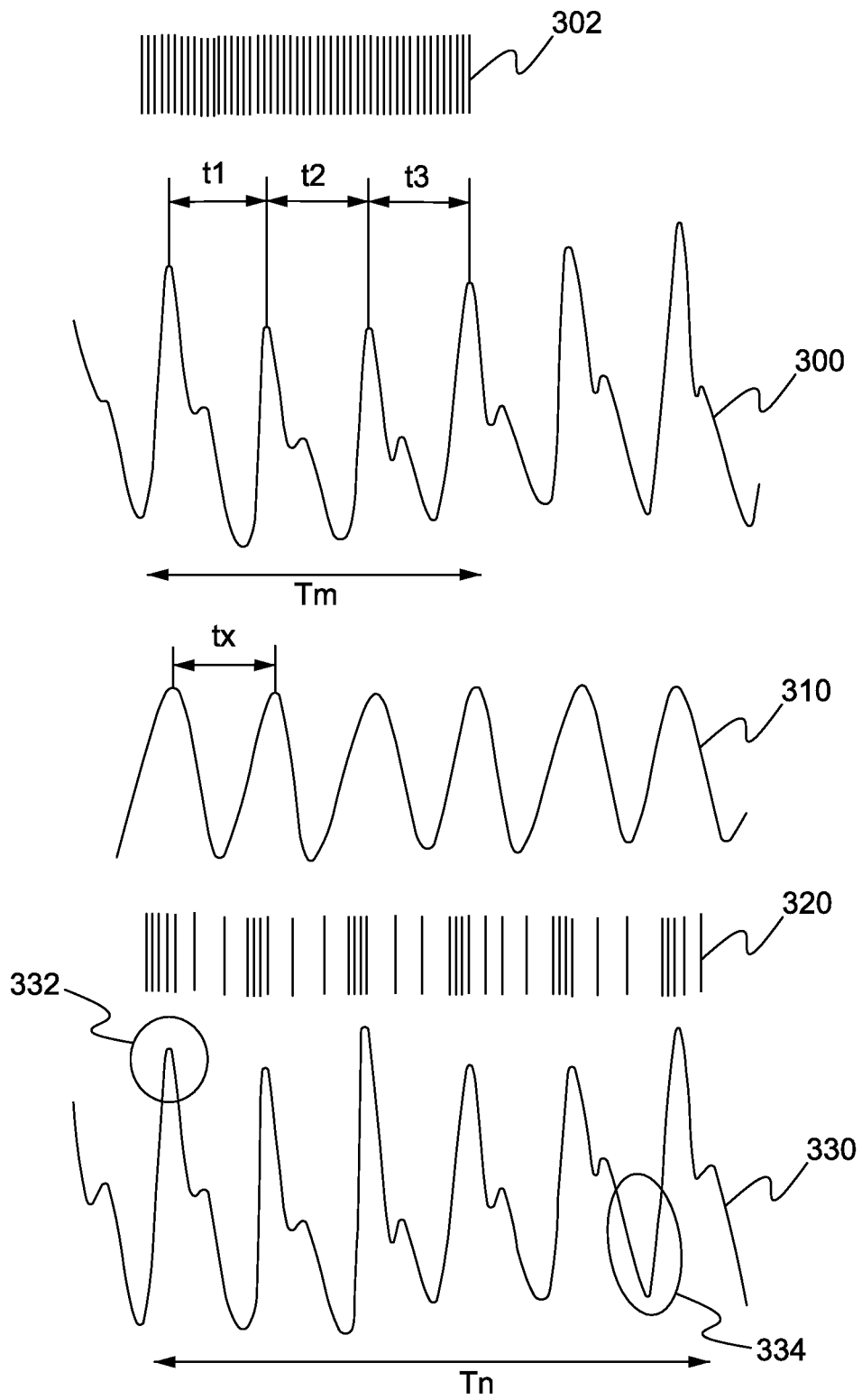
FIG. 3 is a schematic illustration of various stages involved in the photoplethysmogram measurement by the apparatus of FIG. 1, in accordance with an embodiment of the present disclosure.

Referring now to FIG. 3, is a schematic illustration of various stages involved in a PPG measurement by the apparatus of FIG. 1, in accordance with an embodiment of the present disclosure.

As shown, a PPG 300 (a measured pulse waveform) is measured for a first time period 'Tm'. The first time period 'Tm' should be long enough to yield or present a well-defined and consistent form factor of the PPG 300. Further, during the first time period a sampling rate 302 (number of times the at least one photon source is illuminated) should be sufficient to present the well-defined and consistent form factor of the PPG 300. The sampling rate 302 is illustrated with the lines, each line representing a number of time the at least one photon source is illuminated during the first time period 'Tm'.

The form factor of the PPG 300 is used to determine an IBI of the user. As shown, the IBI can be t1, t2, t3, i.e. a time period between the two peaks in the PPG 300 (measured pulse waveform). Therefore, for the first time period 'Tm' the IBI can be t1+t2+t3/3(an average IBI).

Further, using the IBI a parameter is determined for a probability function 310 related to the form factor. Specifically, the probability function 310 is related to where it is likely to have peaks of the PPG 300. As shown, the probability function 310 is periodic in nature (for example a sine wave), and accordingly has a frequency, i.e. f=1/[(t1+t2+t3)/3] for the first time period 'Tm'. Further, the probability function 310 can have a time period, i.e. a peak to peak time, tx=(t1+t2+t3)/3.

The parameter of the probability function 310 is selected to result more samples to be taken from peaks of a PPG compared to other parts of the PPG. Specifically, the probability function 310 is used to determine a sampling rate 320, number of samples to be taken based on a waveform of the probability function 310. The number of samples is associated with the number of times the at least one photon source should be illuminated for the measurement of the PPG 330. Specifically, the sampling rate 320 is determined for a subsequent time period, i.e. a second time period 'Tn' for measurement of the PPG 330.

As shown, the probability function 310 has a higher value around likely peaks as compared to other areas of a pulse waveform thereof. Therefore, the sampling rate 320 takes more samples around peaks 332 as compared to other areas, such as bottom and middle 334 of the PPG 330 during second time period 'Tn'. The sampling rate 320 is shown with lines, which are unevenly spaced apart from each other. For example, more lines are shown corresponding to the peaks of the probability function 310 as compared to the other parts of the probability function 310. This way a sufficient amount of measurements or samples are collected for the peaks 332 ('interesting portion', which enables in deriving the heart rate of the user) as compared to the bottom 334 ('non-interesting portion', which is not used in deriving the heart rate of the user).

Figure 4:
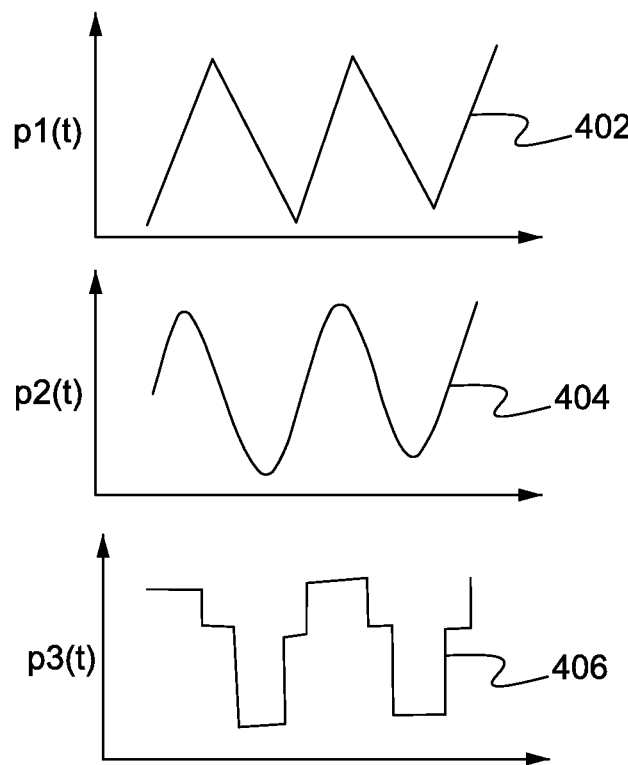
FIG. 4 is a schematic illustration of various waveforms of probability functions related to inter beat interval, in accordance with various embodiments of the present disclosure.

Referring, now to FIG. 4, is a schematic illustration of various waveforms of probability functions related to inter beat interval of the user, in accordance with various embodiments of the present disclosure. Specifically, FIG. 4 illustrates probability distributions p1, p2 and p3, i.e. probability functions based on the IBI of the user. For example, based on the changing IBI the probability distributions can have various form factors. As shown, the probability function p1(t) (i.e. probability distributions on a time-domain for likely peaks of the PPG) is based on the IBI of the user has a triangular waveform 402, similarly the probability function p2(t) has a sinusoidal waveform 404 and the probability function p3(t) has a arbitrary shape waveform 406.

Figure 5:
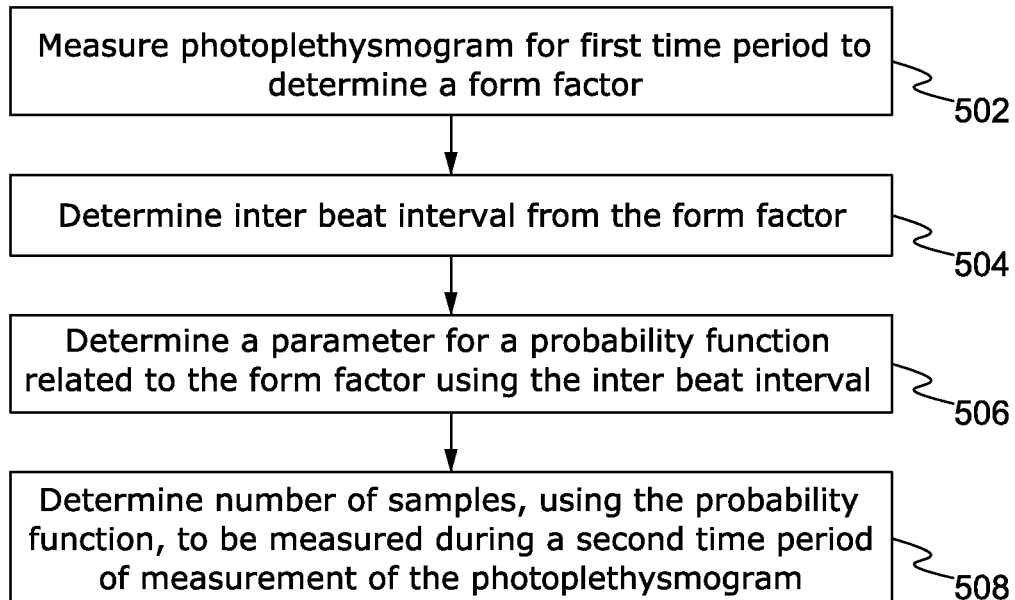
FIG. 5 is an illustration of steps of a method for measuring photoplethysmogram, in accordance with an embodiment of the present disclosure.

Referring now to FIG. 5, illustrated are steps of a method 500 for measuring photoplethysmogram, in accordance with an embodiment of the present disclosure. Specifically, the method 500 illustrates the steps for measuring photoplethysmogram using the apparatus 100, explained in conjunction with the FIGS. 1-4.

At step 502, photoplethysmogram is measured for a first time period to determine a form factor.

At step 504, an inter beat interval is determined from the form factor.

At step 506, a parameter is determined for a probability function related to the form factor using the IBI. The parameter of the probability function is selected to result more samples taken from peaks of the photoplethysmogram compared to other parts of the photoplethysmogram.

At step 508, using the probability function to determine number of samples to be measured during a second time period of measurement of the photoplethysmogram.

The steps 502 to 508 are only illustrative and other alternatives can also be provided where one or more steps are added, one or more steps are removed, or one or more steps are provided in a different sequence without departing from the scope of the claims herein. For example, the method 500 further comprises dynamically biasing DC offset during a time period when photoplethysmogram signal is relatively low changing. Further, the IBI of the step 504 is adjusted based on measurements done during the second time period. Moreover, the measurements during the second time period are filtered using the probability function.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

What is claimed is:

1. A method for measuring photoplethysmogram comprising:
   measuring, from a user and by a wearable device, the photoplethysmogram during a first time period by taking a first number of samples;
   determining an inter beat interval from the photoplethysmogram;
   using the inter beat interval to determine a binary probability function, wherein the binary probability function determines a distribution of a second number of samples to be taken during a second time period of measurement of the photoplethysmogram; and
   using the binary probability function to determine a sampling rate for the second number of samples to be taking during the second time period of measurement, wherein the sampling rate comprises instructions to perform measurements of one or more portions of the photoplethysmogram during the second time period of measurement.

2. The method of claim 1, further comprising:
   using a form factor for determining the binary probability function.

3. The method of claim 2, wherein the binary probability function is determined to result in more samples taken from peaks of the photoplethysmogram compared to other parts of the photoplethysmogram.

4. The method of claim 1, further comprising:
   dynamically biasing direct current offset during an off-peak time period of the photoplethysmogram.

5. The method of claim 1, further comprising:
   adjusting the second number of samples to be taken during the second time period of measurement of the photoplethysmogram and the distribution of the second number of samples to be taken in function of time, if the inter beat interval changes.

6. The method of claim 1, wherein measurement results during the second time period of measurement are filtered using the binary probability function.

* * * * *